United States Patent [19]

Leysieffer et al.

[11] Patent Number: 5,277,694
[45] Date of Patent: Jan. 11, 1994

[54] ELECTROMECHANICAL TRANSDUCER FOR IMPLANTABLE HEARING AIDS

[75] Inventors: Hans Leysieffer, Taufkirchen; Guenter Hortmann, Neckartenzlingen; Joachim Baumann, Munich, all of Fed. Rep. of Germany

[73] Assignee: Implex GmbH, Neckartenzlingen, Fed. Rep. of Germany

[21] Appl. No.: 834,845

[22] Filed: Feb. 13, 1992

[30] Foreign Application Priority Data

Feb. 13, 1991 [DE] Fed. Rep. of Germany ....... 4104358

[51] Int. Cl.$^5$ ............................................. H04R 25/00
[52] U.S. Cl. ..................................... 600/25; 381/68.3; 181/130
[58] Field of Search ............ 600/25; 128/420.5, 420.6; 623/10-11; 181/126-137; 381/68-69.2

[56] References Cited

U.S. PATENT DOCUMENTS

| | | |
|---|---|---|
| 3,594,514 | 7/1971 | Wingrove . |
| 3,712,962 | 1/1973 | Epley . |
| 3,764,748 | 10/1973 | Branch et al. . |
| 3,870,832 | 3/1975 | Fredrickson . |
| 3,882,285 | 5/1975 | Nunley et al. . |
| 4,150,262 | 4/1979 | Ono . |
| 4,606,329 | 8/1986 | Hough . |
| 4,729,366 | 3/1988 | Schaefer . |
| 4,756,312 | 7/1988 | Epley . |
| 4,988,333 | 1/1991 | Engebretson et al. . |
| 5,015,224 | 5/1991 | Maniglia . |
| 5,015,225 | 5/1991 | Hough et al. . |

FOREIGN PATENT DOCUMENTS

| | | |
|---|---|---|
| 242038 | 10/1987 | European Pat. Off. . |
| 263254 | 4/1988 | European Pat. Off. . |
| 341902 | 11/1989 | European Pat. Off. . |
| 2825233 | 1/1979 | Fed. Rep. of Germany . |
| 3617118 | 10/1989 | Fed. Rep. of Germany . |
| 3918086 | 9/1990 | Fed. Rep. of Germany . |
| 1440724 | 6/1976 | United Kingdom . |
| 2176078 | 12/1986 | United Kingdom . |
| 2188209 | 9/1987 | United Kingdom . |

OTHER PUBLICATIONS

Adv. Audiol., vol. 4, pp. 23-43; 51-72 and 107-116 (Karger, Basel 1988).
Arch Otolaryngol Head Neck Surg.-vol. 113, Aug. 1987 *Implantable Hearing Aid,* Naoaki Yanagihara, MD et al., pp. 869-872.

*Primary Examiner*—Lee S. Cohen
*Assistant Examiner*—J. P. Lacyk
*Attorney, Agent, or Firm*—Sixbey, Friedman, Leedom & Ferguson

[57] ABSTRACT

Electromechanical transducer for implantable hearing aids. The transducer has a hermetically sealed and biocompatible housing, in which a wall is designed as a membrane that can oscillate, and which forms a heteromorphic connecting element together with a piezoelectric ceramic disk. Mechanical oscillations of the housing membrane are coupled to the middle ear or inner ear of the user by a mechanically rigid element attached in the central area of the membrane. This element is configured as a bow, so that in positioning the transducer housing from the direction of the mastoid adjoining the tympanic cavity, it acts as an artificial anvil to which coupling elements can be attached for mechanically transmitting oscillations of this artificial ossicle to the inner ear. Various coupling elements can be used, which correspond to the respective individual pathological situation. The application of the entire transducer system can be performed the operating surgeon having an unobstructed view, without extensive, space-creating interventions in the anatomical conditions of the middle ear.

38 Claims, 5 Drawing Sheets

ELECTROMECHANICAL TRANSDUCER FOR IMPLANTABLE HEARING AIDS

BACKGROUND OF THE INVENTION

This invention relates to an electromechanical transducer for implantable hearing aids for average to severe hearing damage, whose cause is located basically in the inner ear.

Since a hearing impairment is still regarded as a "handicap," today the trend in the development of conventional hearing aids has for many years been up to the limit of the feasible miniaturization of the devices. With regard to this aspect, the "In-the-Ear Devices" (ITE) (e.g., German Offenlegungsschrift 28 25 233) have made good progress and are today more widely used than "Behind-the-Ear Devices" (BTE) (e.g., European Patent 0 341 902). Miniaturization, however, has the following drawbacks:

- distinctly lower acoustic amplification in comparison to BTE devices;
- inadequate sound quality, which is attributable basically to nonlinear distortions at high output sound pressure levels and poor frequency response of the "loudspeakers" (hearing aid receivers); this inferior quality is basically caused by the transducer principle (electromagnetic) and the extremely small design. Both factors hardly allow for more improvements, since here the physical limits have already been more or less reached;
- acoustic feedback "howling," which occurs when the device does not fit tightly into the outer ear canal and with high acoustic amplification;
- despite being placed in the outer ear canal, most devices remain visible; this important aspect is a psychological problem (stigmatization) known for a long time and plays a significant role, e.g., during puberty or at important social or business functions;
- the tight fit of the ITE device, necessary for acoustical reasons, in the outer ear canal causes the unpleasant "locking" effect ("foreign body" in the outer ear canal).

A fully implantable hearing aid with an optimized electromechanical transducer for direct mechanical stimulation of the middle or inner ear, which does not exhibit the above-mentioned drawbacks and moreover has substantial improvements, is suitable in hearing impairments whose cause is located in the inner ear or in higher auditory processing levels and cannot be corrected by surgical measures. Worldwide, the share of such inner ear impairments (offending noises, impairment caused by disease, ototoxic medications, presbycusis, etc.) clearly exceeds (about 80%) the cases of a middle ear defect (disturbance of sound conduction) which can be corrected by surgery.

For said reasons, tests have been made for quite some time to use principles of (inner) ear stimulation other than the reconversion into amplified airborne sound. Here, e.g., the possibilities of partially implantable, electromagnetic systems can be mentioned, in which one of the auditory ossicles in the middle ear (malleus, incus and stapes) is permanently joined mechanically with a very small permanent magnet; a (conventional) ITE hearing device now does not control a hearing aid receiver, but a magnetic induction coil whose alternating field, which corresponds to the acoustical data, stimulates the implanted magnet and thus the ossicle chain to oscillations, which are greater in their amplitude with a suitable system design than in the natural case and thus cause the amplifying effect. In this case, the actuating coil is brought, from outside, as close as possible to the tympanic membrane, to keep the air gap to the implanted magnet to a minimum. Other embodiments consist in the replacement of one of the ossicles (e.g., anvil) with one made from a biocompatible material which sheathes a permanent magnet. Such partially implantable electromagnetic systems are described in the literature, e.g., in Heide et al. (Adv. Audiol., vol. 4, pp. 32-43, Karger, Basel 1988) and documented in numerous patents (U.S. Pat. Nos. 3,870,832; 4,606,329; 4,756,312; 5,015,224; and 5,015,225, German Patent No. 3 617 118 C2; European Patent No. 0 242 038; UK Patent Nos. 1 440 724; and 2 188 209).

In addition, systems are also known which stimulate the inner ear by a body-borne sound (bone) conduction (U.K. Patent No. 2,176,078, partially implantable electromagnetic; and U.S. Pat. No. 4,150,262, nonimplantable piezoelectric).

Most of the above-mentioned processes and devices contain partially implantable transducers to stimulate the middle ear ossicles or, directly, the oval window.

A possible principle of a fully implantable electromechanical transducer for direct mechanical stimulation of the stirrup is described in publications of the Japanese group of Yanigahara and Suzuki et al. (Arch Otolaryngol Head Neck, Surg-Vol 113, 1987, pp. 869-872; Hoke, M. (ed), Advances in Audiology, Vol. 4, Karger Basel, 1988).

In this system, the electromechanically active part consists of a piezoelectric ceramic bending transducer which is designed as a bimorph and directly actuates the head of the stirrup with its free oscillating end by a small coupling element (e.g., made from polyethylene). The mechanically necessary permanent clamping of the other end of this bending transducer is achieved by complicated adjusting rods made from titanium, whose fastening element is bolted to the bone. Tests on humans under local anesthesia show that deviations of the stirrup are achievable with this transducer element in the case of transducer voltages around 1.0 volt, which correspond to equivalent stimulating sound levels of 90-100 dB SPL in the audiologically important frequency range of about 250-4000 Hz and thus really are sufficient for a hearing aid supply. An important additional result of these tests is the confirmed high sound quality and freedom from distortion of this type of stimulation of all test subjects, which is also documented in the result quotas of speech comprehension tests in test subjects with distinct inner ear hearing impairments.

In the above-mentioned publications, it is clearly pointed out that a basic problem in the technical achievement of the described transducer elements is the biocompatible sheathing with long-term stability of the freely oscillating piezoelectric ceramic element, which, moreover, also has to have high electrical insulation values in the range of several MOhm since such ceramic elements have a high electrical impedance because of their low quiescent capacity. A further difficulty consists in the space requirement of such transducer elements and the related positioning mechanisms, which obstruct a safe and reliable application in the middle ear area, taking into consideration the individual fluctuations of the anatomical geometries. Further, an anatomically normal and thus functioning ossicle chain has to be broken to be able to use the above-mentioned transducer element; when the loss or other technical or clinical problems occur, which indicate the removal of the transducer, therefore, a surgical reconstruction of the chain has to be attempted to restore the former state.

A similar process is indicated by Epley (U.S. Pat. No. 3,712,962), who also uses piezoelectric bending transducers with coupling to the stirrup as a transducer, which are designed as a bimorph or use a multilayer technique. Here, the necessity of a suitable sheathing is also pointed out (flexible plastics, silicone); also, an embodiment of coupling elements of the free bending oscillator end to the stirrup is described.

Nunley et al. (U.S. Pat. No. 3,882,285) describe a process, in which, parallel to the anatomically normal and intact ossicle chain, the stirrup or the oval window are directly oscillated by a piezoelectric element to "support" and to amplify the natural method of transmission. A detailed embodiment of the transducer is not indicated. In this connection, it is to be noted that interferences can occur in the case of the nonideal phase frequency characteristic of the deviation of the transducer in comparison to natural transmission, which entail considerable breaks in the overall frequency range and thus can very negatively influence the transmission quality and the amplification.

Similar data is documented in Wingrove (U.S. Pat. No. 3,594,514), who also uses a piezoelectric bimorphic element to stimulate the stirrup or oval window, which is to be embedded on one side permanently in the mastoid bone and exhibits a suitable biocompatible encapsulation. Detailed embodiments or descriptions are not indicated there either.

Additional, varied types of stimulations of the stirrup or oval window with piezoelectric bending transducers in a bimorphic type of construction are also found in Branch et al. (U.S. Pat. No. 3,764,748); detailed embodiments of the possibilities of how such transducer elements can be biocompatibly sheathed and electrically insulated, are not mentioned either.

The most detailed embodiments of suitable transducer processes for fully implantable hearing aids are found in Schaefer (U.S. Pat. No. 4,729,366, European Patent No. A1 0 263 254). Here, a method of hearing improvement and a fully implantable device are described, in which two electromechanical transducers, which also preferably are designed as piezoelectric bimorphic elements, are inserted in the broken chain as an "active link" after an interruption of the ossicle chain (typically by removing the anvil as a link between the hammer and stirrup). One of the transducers performs a microphone function by mechanical coupling to the tympanic membrane or the hammer, and the thus obtained electrical signal is fed by an electronic system amplified to the output transducer. This stimulation transducer in turn also stimulates the stirrup or the oval window.

In the above-mentioned patents of Schaefer, conceivable embodiments of these transducers are described to the effect that, preferably, piezoelectric bending transducers are clamped on one side in housings, not described in more detail, and the coupling of the free, oscillatory end of these transducers to the ossicles, preferably, takes place by a thin wire of stainless steel, and in the output transducer this wire is looped, e.g., around the head of the stirrup. The lateral guiding of this wire by the wall of the housing, which contains the active transducer element, takes place by a guide bushing which is embedded in the housing wall. However, a precise explanation of this embodiment is not indicated. The active transducer elements can be piezoelectric (piezoactive polymers such as PVDF or piezoelectric ceramics, preferably with a bimorphic structure) or electromagnetic.

The above-indicated prior art of fully implantable electromechanical transducers for hearing aids can be summarized as follows:

In almost all publications and patents, the use of piezoelectrically active transducer elements, which are produced only as a bimorphic structure or in a multilayer technique, is proposed. The principle of the bimorph means that two strips of piezoelectrically active material are joined together mechanically so that in simultaneous electrical stimulation of the two elements mechanically permanently clamped on one side, one is shortened because of the piezoelectric transverse effect and the other is correspondingly lengthened, by which a distinctly greater deflection and thus deviation of the free end of this connecting element is achieved than with only one transducer strip. In joining together more than two of these strips (multilayer technique), the producible force can additionally be increased. Largely, optimal use is then made of this principle if the geometry of the connecting elements is designed as rectangular strips, and the achievable deviation with the given transducer voltage is increased with increasing length and decreasing thickness of the connecting elements.

Although other physical transducer principles are mentioned (in particular electromagnetic), it is explained that technically simple transducer elements are achievable only with the piezoelectric effect.

The sound quality achievable with the stimulation of the ossicle chain and in particular of the stirrup directly with the above-mentioned bimorphic elements is apparently very high.

In some patents and publications, references to the necessary biocompatible sheathing and high-grade electrical insulation of these piezoelectric transducer elements are indeed found; detailed embodiments of such transducer designs are, however, if mentioned at all, are only generally indicated.

The experiences of many years with implantable, active human implants, such as pacemakers and cochlea implants, show that such systems have to be hermetically sealed, to meet the requirement of clinical safety and a long service life. The concept of hermetic sealing is mentioned, however, in none of the above-mentioned patents; in particular, no implantable hearing aid with a transducer design is described as being hermetically sealed.

Nor is it described how such a transducer design has to be made, so that the transducer also is actually implantable, i.e., is configured so that the operating surgeon retains a substantially free view of the operating area (in particular of the ossicle chain and the oval and round window); further, the transducer has to be designed so that its application in the middle ear area is possible under the given anatomical conditions, and no substantial surgical curettage has to be performed, which is expensive and entails the high risk of traumatic reactions and subsequent infections. This aspect contradicts the use of piezoelectrical bimorphic transducer elements, since the latter—as mentioned—have to be technically optimally extended and require a permanent clamping of one end (minimum useful length about 7 mm; this measurement already exceeds anatomically average geometries in the middle ear). Such design features are also not indicated in any patent.

Direct transducer material data for piezoelectric elements relates only to concepts such as "piezoelectrically active ceramic" or PVDF (polyvinylidene fluoride).

Attempts at solving full encapsulation of implantable hearing aid transducers are indicated only in two of said patents (U.S. Pat. No. 4,988,333 and German Patent No. 3 918 086). Here, active transducer elements in closed housings are used, whose electrically stimulated mechanical oscillations are decoupled by hose lines; the oscillations are further conveyed in these hose lines in liquid or gaseous media and guided either to the head of the stirrup or directly by a liquid coupling through the oval or the round window into the perilymph of the cochlear basal turn. A significant advantage of this special hydromechanical coupling (German Patent No. 3 918 086) consists in that sizable deviations in comparison to the driving transducer membrane, and thus high equivalent output sound pressure levels, are achievable on the basis of the hydraulic principle at the end of the coupling element. Questions of germ-free filling with liquid and of the long-term stable coupling to the middle or inner ear are problematical here with respect to the technical implementation.

SUMMARY OF THE INVENTION

This invention has as its primary object to provide an electromechanical transducer for direct mechanical stimulation of the middle/inner ear for fully implantable hearing aids, which improves the known prior art to the effect that, on the one hand, the above-mentioned drawbacks of the documented transducer methodologies are avoided, and on the other hand, the operating properties of the transducer make possible a high sound quality and sufficient sound pressure levels for adequate hearing aid supply.

An electromechanical transducer for implantable hearing aids for direct mechanical stimulation of the middle or inner ear according to the invention features a hermetically sealed and biocompatible housing, in which a housing wall is made as a membrane that can oscillate, and forms an electromechanically active heteromorphic connecting element with a piezoelectric ceramic disk applied to the inside. The mechanical oscillations of this element are transmitted by a mechanically rigid bow and a mechanically rigid coupling element (that is permanently attached to the outside of the membrane) to a middle ear ossicle or directly to the inner ear.

According to the invention, the above-mentioned object is achieved in that a piezoelectrically active element is placed in a fully encapsulated, hermetically sealed and biocompatible housing so that this piezoelectric element is in direct mechanical connection with a wall of the encapsulated housing made of thin material and this housing wall acts as an active oscillating membrane, whose oscillations are further conveyed to the middle or inner ear by a mechanically rigid coupling element permanently attached on the outside of this membrane.

In this case, the central point of the invention is the principle of a hermetically sealed, piezoelectric heteromorphic transducer, which converts the electronically amplified (audio) signals into mechanical oscillations and further conveys the latter directly to the middle or inner ear, without retransformation into acoustic signals.

In the transducer design according to the invention, the piezoelectric transverse effect is used as in a bimorphic element, only the partner of the connection does not consist here of a second piezoelectrically active element, but of a passive, metallic membrane of a geometry similar to that of the piezoelectric element. Such connecting elements are called piezoelectric heteromorphic transducers and are now widely used, e.g., as acoustic signal transmitters in personal computers. Such transducer elements are mostly circular, piezoelectric ceramic disks, which are coated on both sides with very thin, electrically conductive materials, which are used as electrode surfaces. These piezoelectric disks are mechanically permanently connected on one side with metallic membranes (mostly brass) of approximately the same thickness, but larger diameters using electrically conductive adhesives. If an electric field is applied to the piezoelectric disk by the two electrode surfaces (the metallic membrane is a connection in this case of application), the disk changes its geometry, preferably in the radial direction, because of the transverse piezoelectric effect (transverse effect). But, since an expansion or radial shortening is prevented by the mechanically permanent connection with the passive, metallic membrane, a deflection of the connecting element is produced, which with appropriate positioning of the disk edge is at a maximum in the center. This principle of the piezoelectric heteromorphic transducer can advantageously be used for the solution of these problems.

These and further objects, features and advantages of the present invention will become apparent from the following description when taken in connection with the accompanying drawings which, for purposes of illustration only, show several embodiments in accordance with the present invention.

DETAILED DESCRIPTION OF THE PREFERRED EMBODIMENT

Figure 1:
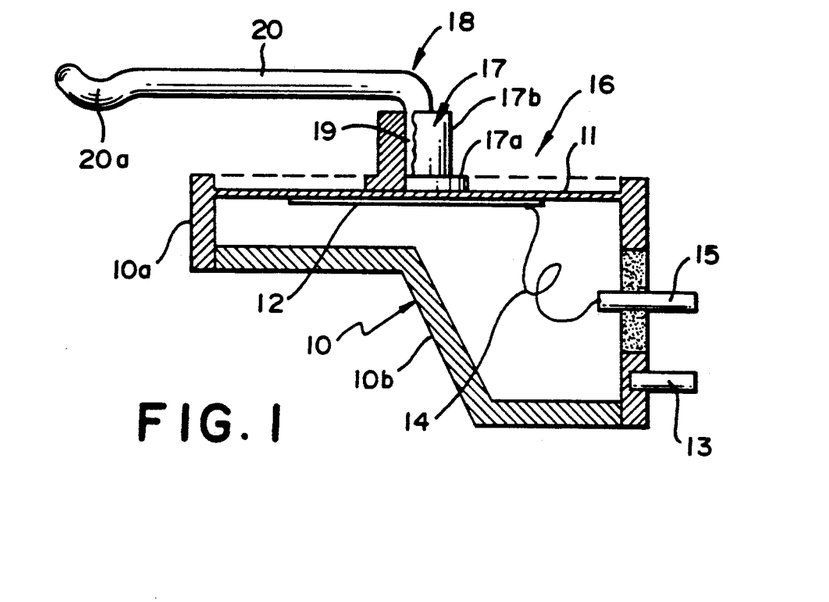
FIG. 1 is an enlarged diagrammatic section through an electromechanical transducer designed according to the invention.

In the embodiment illustrated in FIG. 1, a metallic, biocompatible housing 10 that is hermetically sealed on all sides has a top side formed of a, preferably circular, thin membrane 11 that can oscillate. The inner side of membrane wall 11 is mechanically, permanently connected with an also preferably circular piezoelectrically active ceramic disk 12 using an electrically conductive adhesive (e.g. LOCKTITE Type 366 glue with LOCK-TITE Type 760 activator). The diameter of ceramic disk 12 is smaller than the diameter of housing membrane 11. The arrangement formed by housing wall 11 and ceramic disk 12 represents an electromechanically active heteromorphic connecting element. The surfaces of piezoelectric disk 12 are coated, thinly in comparison to the thickness of the disk, with an electrically conductive material to serve as electrodes. An electrical terminal (ground) 13 is directly attached to the metallic, and thus electrically conductive, housing 10. The counter-electrode surface, on the underside of piezoelectric disk 12, is bonded to a thin, flexible wire 14 (e.g., using conventional bonding techniques). Wire 14 is connected to a hermetically sealed and electrically insulated, electrical terminal 15, and it, thus, forms the second (signal or active) electrical connection of the transducer which designated, generally, by reference numeral 16. Transducer housing 10 consists, including housing membrane 11, of a biocompatible material, preferably titanium, niobium, tantalum or their alloys, or of another biocompatible metal. However, it can be produced, at least partially, from a body-compatible ceramic material, for example, $Al_2O_3$. Housing 10, suitably, has a diameter in the range of 6 to 13 mm, preferably about 9 mm. Piezoelectric ceramic disk 12, i.a., can consist of lead-zirconate-titanate (PZT) of a thickness that is, suitably, about the same as the thickness of membrane 11. The thickness of membrane 11 and ceramic disk 12 are advantageously each in the range of 0.05 to 0.15 mm. In the case of the circular design of heteromorphic connecting element 11,12, the radius of housing membrane 11 should be greater than the radius of piezoelectric ceramic disk 12 by a factor of 1.2 to 2.0. A factor of about 1.4 has proven especially advantageous.

If an electric voltage is placed on both electrical terminals 13, 15 by an electronic unit E (FIG. 8) by leads 21, a radial change of geometry of piezoelectric disk 12 is produced, which results in a deflection of the hetero-connection of the piezoelectric ceramic-metal membrane and thus to a deviation of metal membrane 11. Because of the hard-edged clamping (velocity equals zero) of the membrane, the membrane deviation is at a maximum in the center.

A circular flange 17a of flange member 17 is mechanically, permanently attached to the outer side of housing membrane 11 at its center (e.g., by welding or with biocompatible adhesives). The diameter of flange 17a is significantly smaller than the diameter of the membrane 11. Short leg 19 of a basically L-shaped, thin bow 18 is mechanically permanently connected with flange member 17, such as by being fixed in an upstanding socket portion 17b thereof. Virtually immediately after coming out from socket portion 17b of flange member 17, bow 18 is bent at a right angle so that a longer leg 20 thereof runs at least approximately parallel to the membrane 11. Long leg 20 of bow 18 is slightly longer than the radius of the cylindrical sidewall 10a of the housing 10, so that it slightly projects radially beyond the housing surface 10a, preferably by about 2 mm. Bow 18 is configured structurally and consists of such a material that as high as possible a mechanical rigidity with as low as possible a weight is achieved. In particular, bow 18 is made from a solid or hollow wire, or a carbon fiber reinforced composite material is produced with a high elasticity modulus. The diameter of bow 18 is suitably in the range of 0.25 to 1.0 mm and is preferably about 0.5 mm.

Bow 18, by the deflection of housing membrane 11, performs a movement perpendicular to it as a result of permanent mechanical coupling of flange member 17 to housing membrane 11. The deflection of housing membrane 11, and thus the perpendicular movement of bow 18, follow the chronological course of the voltage applied to connecting terminals 13, 15 of transducer 16 because of the electromechanical transformation of piezoelectric element 12. Consequently, the audio signals received and electrically converted by a microphone M (FIG. 8) result, after an electronic amplification in the electronic unit E, directly in mechanical movements which correspond to the acoustical data. These perpendicular movements of bow 18 are further conveyed to the ossicle chain of the middle ear or to the stirrup or the oval or round window or else to an artificial window by mechanical coupling elements, which can be permanently attached to the slightly bent, somewhat hook-like outer end 20a of long leg 20 of bow 18. They thus produce the audiological amplifying effect in the case of an appropriate design of the preprocessing electronic system.

The dimensioning of the connecting element of piezoelectric disk 12/metal membrane 11 with mechanically permanently attached bow 18 is preferably designed so that the dynamic masses per unit of area and rigidities produce a dominant resonant frequency (mode 0/0) in the range of 6 to 12 kHz, preferably about 10 kHz, i.e., a first mechanical resonant frequency which is at the upper limit of the desired transmitting range (for example, about 100 Hz to 12 kHz). This means that the system is tuned at or above the high end of the audiologically important frequency range. This has, on the one hand, the significant advantage that in the low to medium frequency range, a flat frequency curve of the transducer movement, and thus ideal transmitting properties, are achieved. On the other hand, an increase of the transducer movement, in the case of unchanged transducer voltage, is produced by the low side of the resonance magnification factor, which still lies in the transmitting range. Thus, high stimulation levels are available especially in the frequency range, in which according to experience, most impaired hearing of the inner ear begins and/or is most pronounced. In addition, the subjective perception of the sound level is greater in this upper frequency range, since the frequency curve of the natural stirrup deviation decreases greatly from about 1 kHz with increasing frequency (for example, Gyo, K. and Goode, R. L.: "Measurement of Stirrup Vibration Driven by the Ceramic Vibrator of a Middle Ear Implant—Human Temporal Bone Experiments," Adv. Audiol., vol. 4, pp. 107-116, Karger, Basel 1988).

From the diagrammatic transverse section of transducer 16 in FIG. 1, it can be seen that housing 10, which is filled with a noble gas, for example, argon, is designed in the shape of a cylindrical disk only in the area of housing membrane 11. The opposite end (i.e., lower part) of housing 10 relative to the membrane 11 being step-like with a deeper area being connected to a shallow area by a sloping housing wall 10b, the shallow area being under bow 8. It can be seen from FIG. 1 that the hermetically sealed contact bushing for active electrical terminal 15 of piezoelectric element 12 is in the deeper housing area.

Figure 2:
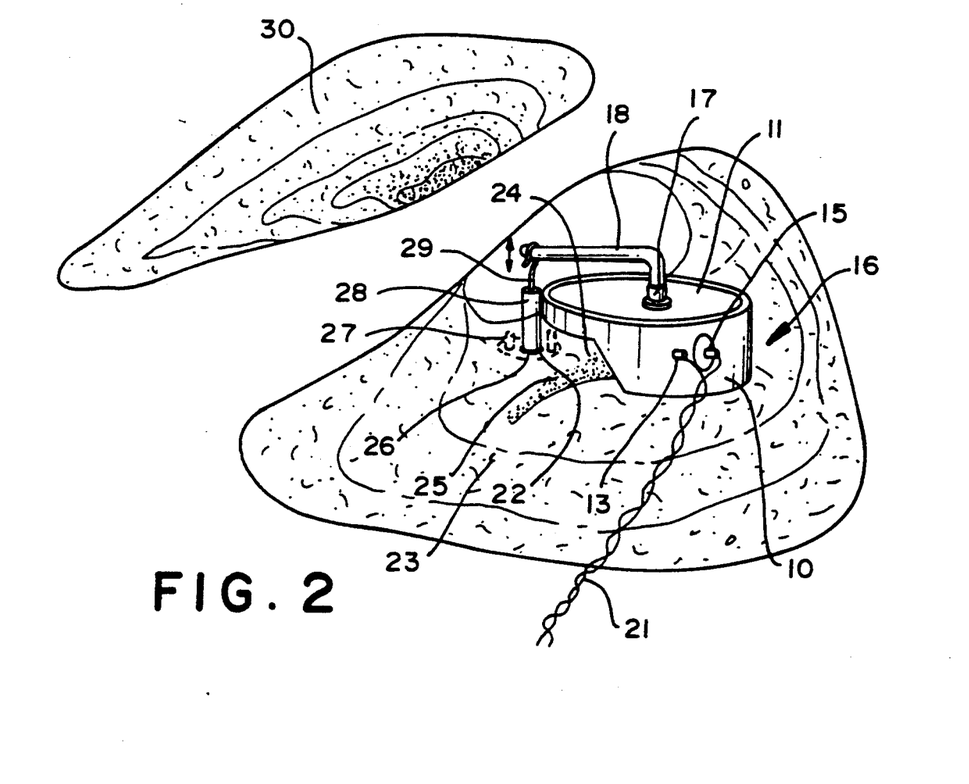
FIG. 2 shows the use of the electromechanical transducer for direct inner ear stimulation through the oval window.

This step-like design of the lower part of transducer housing 10 also has a second reason, which can be seen from FIG. 2, which represents the position of transducer 16 and a possible coupling shape for direct stimulation of the inner ear via the oval window 22. In this representation, it can be seen that transducer housing 10 is not placed in the middle ear (tympanic cavity), but is in an area which is accessible from the mastoid. Here, after opening the mastoid, in an artificial mastoid cavity, the transducer is guided to the antrum, so that the lengthwise axis of the bent bow part points in the direction of the middle ear. The circular membrane area sits here on a bony wall 24 over facial nerve canal 25, or the horizontal semicircular canal, while the deeper part of transducer housing 10 rests on the bottom of mastoid cavity 23. The shape of the transducer is optimized, so that in this position of transducer housing 10, the slightly curved end of bow 18 sits as tightly as possible over or beside the stirrup head, so that different types of mechanical elements for coupling to the ossicle chain or directly to the inner ear can be applied. The coupling of the oscillating transducer part to the middle ear or to the inner ear is possible with the operating surgeon having an unobstructed view, e.g., through the outer ear canal.

In FIG. 2, for reasons of clarity, the auditory ossicles are left out except for stirrup base 26 and the partial showing of stirrup leg 27. As an example, for the direct inner ear stimulation via oval window 22, a conventional stirrup prosthesis 28 can be used as a coupling element, which is inserted after opening stirrup base 26 and attaching its metal fastening eyelet 29, not to the natural anvil, but to the curved end of transducer bow 18.

Figure 8:
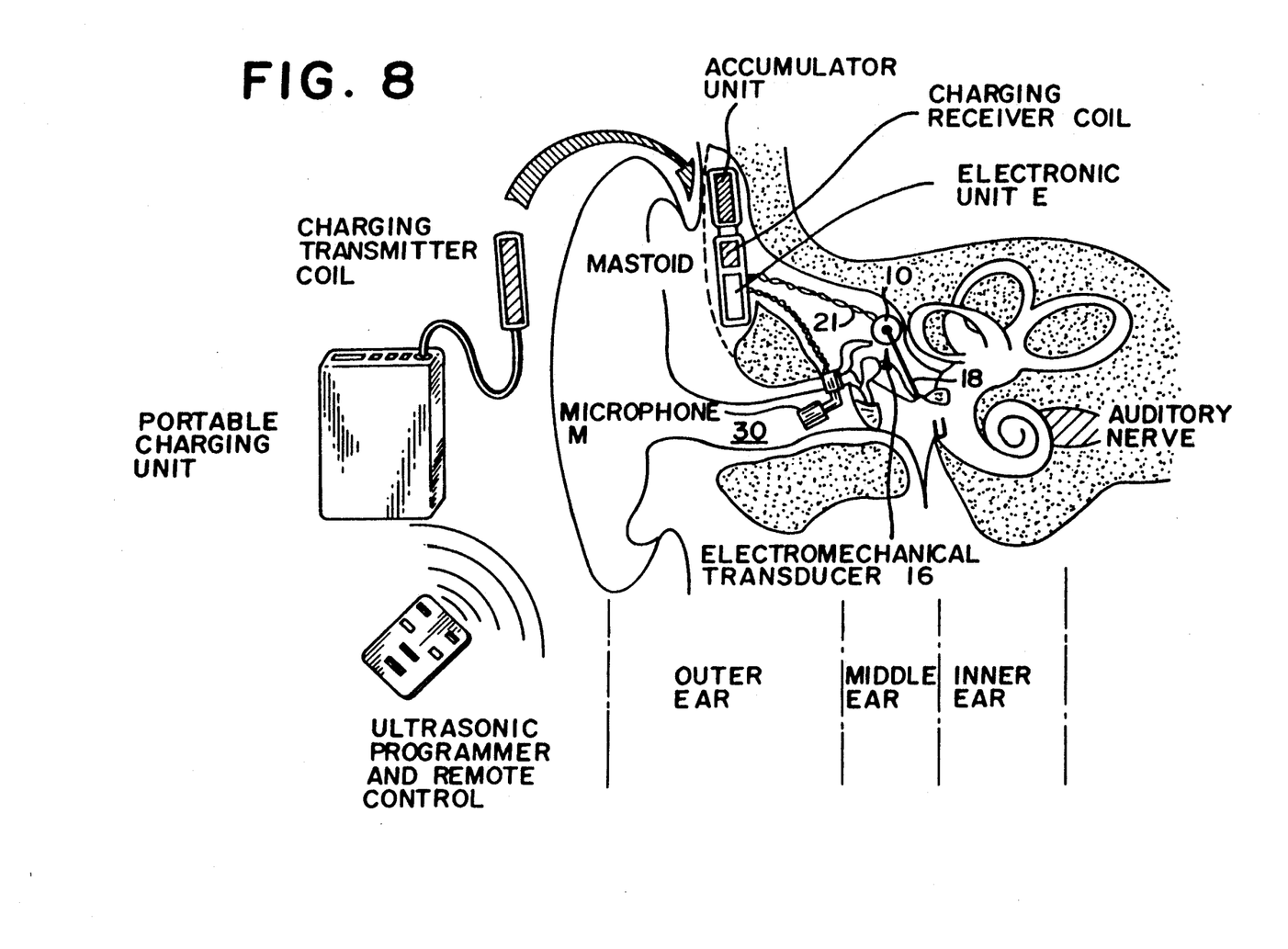
FIG. 8 schematically depicts a hearing aid system utilizing the transducer of the present invention implanted in a user's ear.

A great advantage of this transducer embodiment lies in the fact that the application of the coupling elements and their coupling to the middle ear/inner ear can take place under full and direct view of the operating surgeon through the outer ear canal indicated in FIGS. 2 & 8 at 30. Another advantage is the space of the middle ear (tympanic cavity) largely remaining free from foreign bodies of large volume.

After optimal positioning with a biocompatible adhesive material, in particular bone cement, the attaching of transducer housing 10 can take place. An advantageous embodiment is also a coating of the transducer housing underside, including its step, with bioactive ceramics (e.g., hydroxylapatite), which make possible a permanent growing in and thus the long-term stable positioning of transducer 16.

Figure 3:
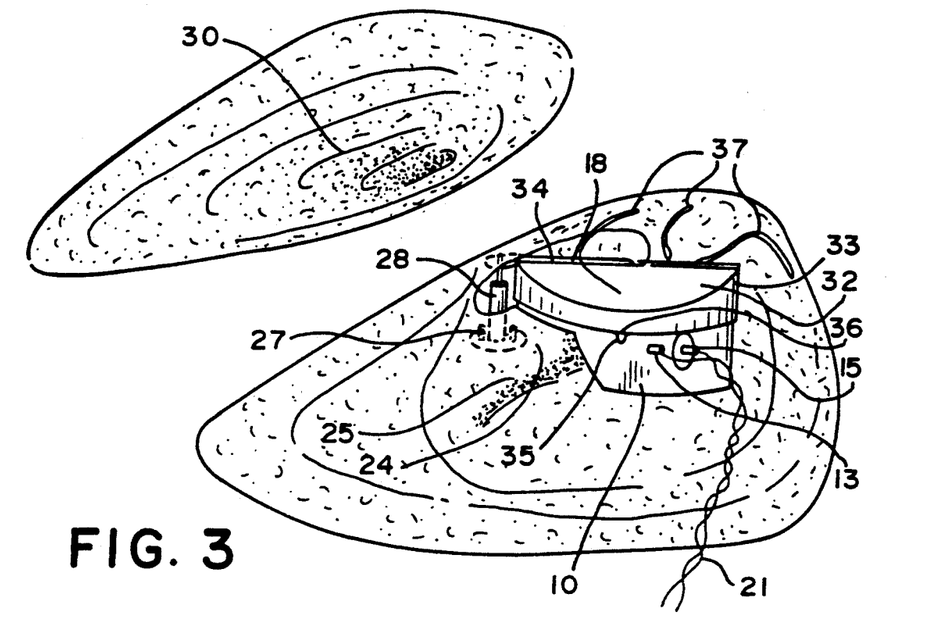
FIG. 3, in an arrangement similar to FIG. 2, shows a modified type of attachment of the transducer housing at the implantation point.

Another type of attachment of transducer 16 is represented in FIG. 3. There, the top of transducer housing 10 (membrane 11 with joined bow 18) is enclosed by a cover 33 which rests on the edge of the upper edge of the transducer and that has a pair of oppositely sloping in wall portions 32. Bow 18 runs, in this case, in a U-shaped slit 34 in this cover 33, and it is thus largely mechanically protected. Cover 33, that can be slipped on from above, is locked in position on transducer housing 10, for example, by interaction of a groove 35 in the housing edge with a lug 36, engaging in groove 35, on cover 33. On the upper surface, cover 33 has two or more, deformable, preferably wire-shaped, rigid clamps 37, which suitably consist of platinum, titanium, niobium or their alloys, or of high-grade steel. In FIG. 3, three such clamps 37 are represented. Clamps 37 are configured so that they allow for the insertion of transducer 16 from the mastoid in the just mentioned way and can be spread out after final positioning so that a bracing on the superimposed bone will takes place at two or more points, so that transducer housing 10 is pressed downward and obliquely in the direction of the middle ear and thus rests permanently on bony wall 24. In addition, a stabilization can take place with the above-indicated methods (bone cements, bioactive ceramic coatings).

Another advantage of housing cover 33 is the protecting and thus damping action on sound waves, which are radiated to a certain extent by oscillating housing membrane 11 and which, with high amplification factors, can lead possibly to feedback problems with the sound-absorbing microphone, when this microphone or a corresponding acoustical feeder to the microphone is positioned near transducer 16.

Figure 4:
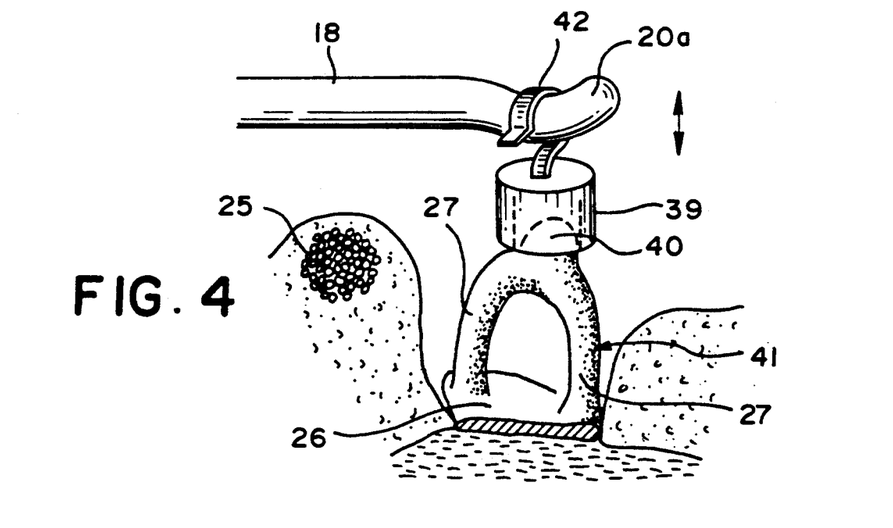
FIG. 4 is an enlarged depiction of the design of a coupling element on the stirrup head.
Figure 5:
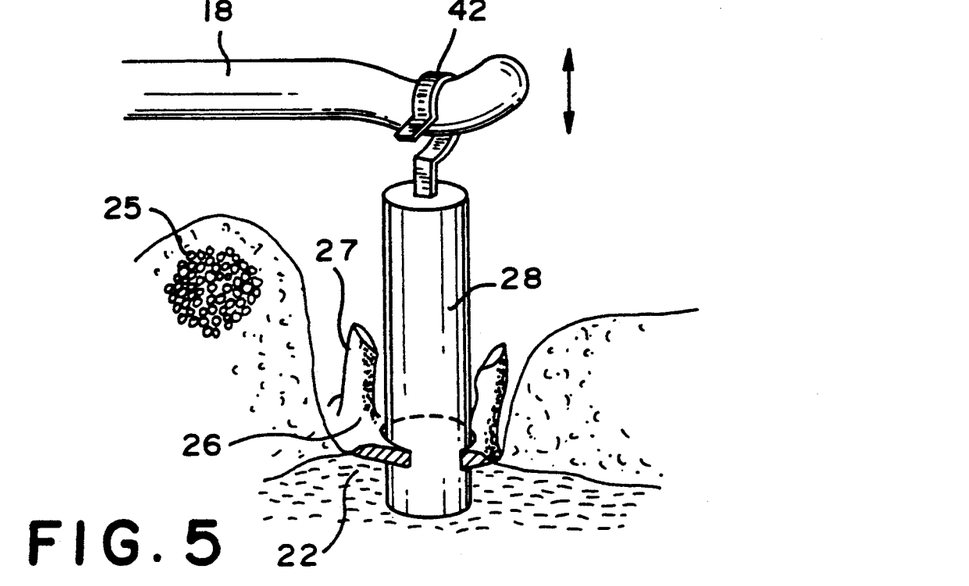
FIG. 5 illustrates the use of a coupling element for direct inner ear coupling by the oval window.
Figure 6:
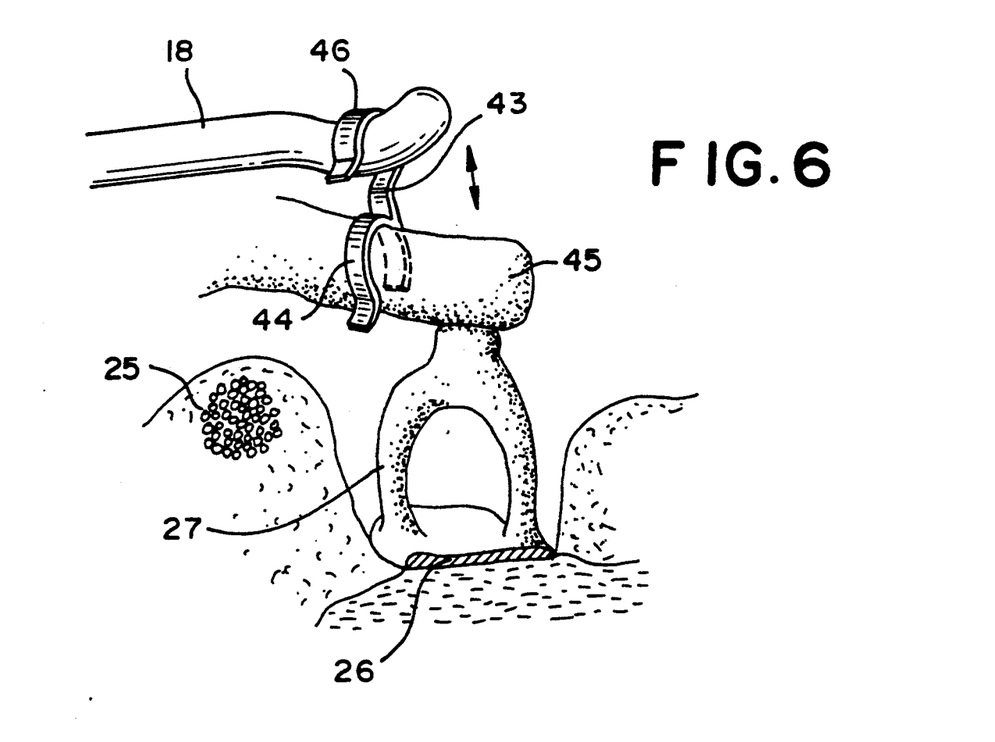
FIG. 6 shows a coupling to the natural anvil with the anvil-stirrup joint intact.

In FIGS. 4 to 6, possible manners for coupling of the projecting end of vertically oscillating membrane bow 18 are represented on the ossicle chain or directly on the inner ear. In this case, it is expressly to be pointed out that, for the application of the described transducer, the auditory ossicle chain does not necessarily have to be interrupted. To avoid interferences, which can result from the additional natural oscillation of the ossicle chain by sound waves striking the tympanic membrane from the outside, an immobilization of the chain, for example by mechanical attachment of the hammer head, is entirely sufficient. Care has only to be taken that the subsequent ossicles (anvil and stirrup) remain mobile, if a coupling to these ossicles is to take place.

In FIG. 4, an embodiment of a coupling element to the stirrup head is represented after natural or artificial interruption of the ossicle chain (e.g., absence or removal of the anvil). A small sleeve 39, made from biocompatible material (for example, polyethylene, polytetrafluoroethylene or hydroxylapatite), is slipped on head 40 of the stirrup designated 41 as a whole, and is connected with the other end by a thin metal strip 42 of a type used in conventional stirrup prostheses (for example, made from platinum, platinum alloys or stainless steel) by substantially looping it around the slightly curved end 20a of transducer bow 18. The simple and secure positioning of this coupling element is possible by first looping strip 42 around bow 18 in a loose manner. The permanent mechanical connection to bow 18 can then take place by pressing shut metal strip 42 or by application of a drop of adhesive (e.g., medical grade silicone).

FIG. 5 shows a suitable method of direct inner ear coupling via oval window 22 by using a standard, commercially available, stirrup prosthesis 28. This type of coupling makes possible the common methodology of strapedectomy with hollowing or removal of base 26 and insertion of a prosthesis 28 which, now, is not attached to the natural anvil but, again, is looped over the end of transducer bow 18. The positioning and attachment of coupling element 28 takes place as described above.

FIG. 6 represents a methodology of coupling to the natural anvil in an intact anvil-stirrup joint after immobilizing the ossicle chain inlet (hammer head). A coupling link 43, formed in the manner of a double hook, has a clamp 44 (e.g., a strip suitably made from platinum, platinum alloy or stainless steel) that at least partially surrounds the long anvil projection 45, and may be in the form of the eyelet of a stirrup prosthesis. A second eyelet 46 of coupling link 43 is coupled as described above to transducer bow 18. Thus, approximately the same oscillation direction of stirrup 41 is achieved as in natural stimulation.

Figure 7:
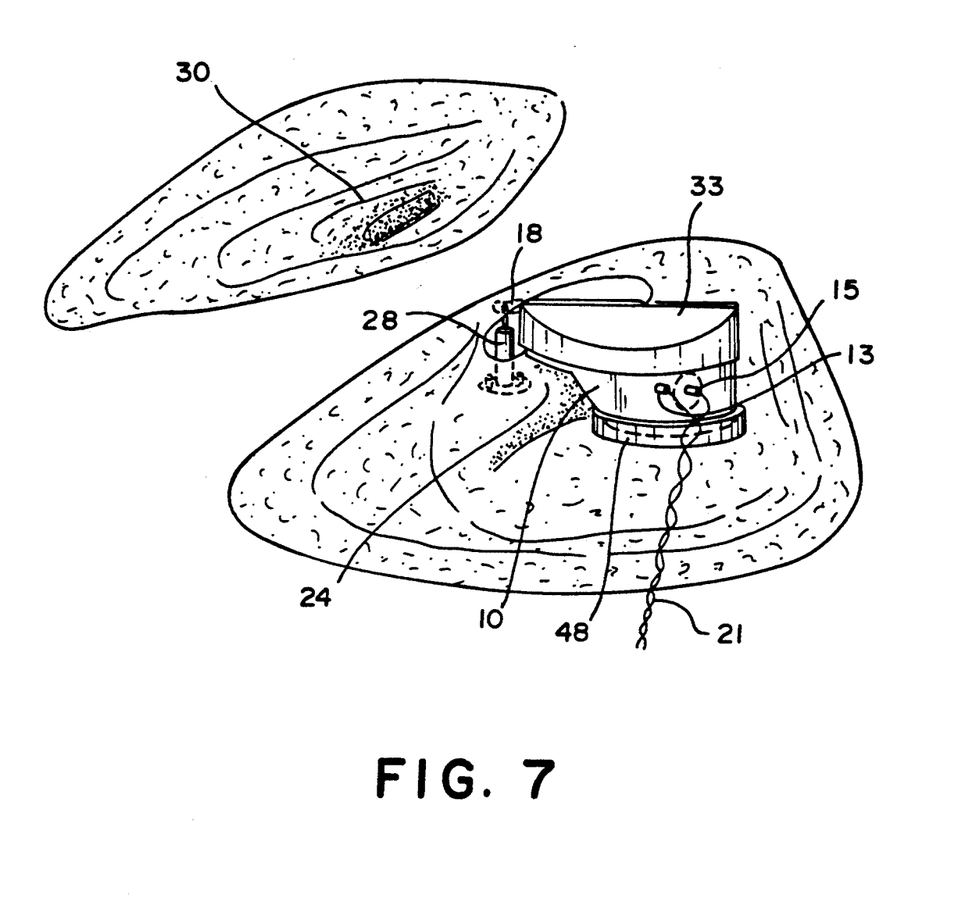
FIG. 7 shows another type of the positioning of the transducer housing.

In the embodiment illustrated in FIG. 7, transducer housing 10 is mechanically solidly and replaceably attached in a holding device 48 that is designed, for example, in a pan-shaped manner. Holding device 48 consists of a bioactive material, which assures a long-term stable, mechanically permanent growing together in the antrum.

In summary, the explained transducer principle involves the use of a hermetically sealed and biocompatible metallic housing, a wall of which is designed as a membrane that is part of a piezoelectric heteromorphic connecting element. The mechanical oscillations of this housing membrane are uncoupled by a permanently attached, mechanically rigid element preferably at the center of the membrane. This element is configured as a bow, so that, in positioning the transducer housing from the mastoid adjoining the tympanic cavity, in shape and local position creates an artificial anvil, to which suitable coupling elements can be attached, and which transmit the oscillations of this artificial ossicle mechanically to the inner ear. In this case, it is taken into consideration that, on the one hand, various coupling elements can be used, which correspond to the respective, individual pathological situation, and that, on the other hand, the application of the entire transducer system can be performed under free view of the operating surgeon without extensive, space-creating interventions in the anatomical conditions of the middle ear.

The above-described piezoelectric heteromorphic transducer was produced in the form of laboratory models and tested on humans in intensive clinical tests. Here, with volunteer patients, who had to undergo a reconstructive middle ear operation under local anesthesia because of slight middle ear defects, the oscillations of the transducer membrane from outside were coupled through the outer ear canal by an extended mechanical coupling element to the ossicles of the middle ear, namely to the anvil with an intact anvil-stirrup joint or to the stirrup or the stirrup base in the case of a defective or absent anvil. The theoretical operating parameters of the transducer theoretically calculated in advance were able to be fully confirmed in these pretests in practice relative to the achievable stimulation level with low electric transducer voltages and achievable sound quality.

FIG. 8 represents, generally, a hearing aid system utilizing the transducer of the present invention and a remotely rechargeable and, optionally, programmable electronic unit, the latter mentioned aspects of which are described in greater detail in commonly assigned U.S. Patent Application Ser. No. 07/834,838 filed on even date herewith. To the extent necessary to complete an understanding of this invention, said co-pending application is hereby incorporated by reference.

While we have shown and described various embodiments in accordance with the present invention, it is understood that the same is not limited thereto, but is susceptible of numerous changes and modifications as known to those skilled in the art, and we, therefore, do not wish to be limited to the details shown and described herein, but intend to cover all such changes and modifications as are encompassed by the scope of the appended claims.

We claim:

1. Electromechanical transducer for implantable hearing aids for direct mechanical stimulation of the ear, comprising a hermetically sealed and biocompatible housing having a housing wall that is formed of a membrane which, together with a piezoelectric ceramic disk that is attached on an inner side of the membrane, forms an electromechanically active heteromorphic connecting element, a mechanically rigid bow permanently attached on an outer side of the membrane, and connected to a mechanically rigid coupling element which is adapted to be connected on one of a middle ear ossicle and inner ear of a user; wherein the bow acts as a means for transmitting mechanical oscillations of the connecting element to the rigid coupling element.

2. Electromechanical transducer according to claim 1, wherein the mechanically rigid bow is attached at least approximately at a center of the membrane.

3. Electromechanical transducer according to claim 1, wherein an upper surface of the transducer housing is formed by said membrane; and wherein said membrane is circular.

4. Electromechanical transducer according to claim 1, wherein a lower part of the transducer housing has a stepped configuration for being positioned in an artificially created mastoid cavity adjoining the tympanic cavity in the antrum of the user with the membrane being near the middle ear ossicles of the user and a step of the stepped configuration of the housing is adapted to sit on a bony bottom of the mastoid cavity, so that the bow is adapted to be attached to said one of the middle ear and the inner ear with as free as possible a view by the operating surgeon.

5. Electromechanical transducer according to claim 1, wherein the transducer housing consists of biocompatible material.

6. Electromechanical transducer according to claim 5, wherein the transducer housing at least partially is comprised of a metallic material.

7. Electromechanical transducer according to claim 6, wherein the metallic material of the transducer housing is selected from the group consisting of titanium, niobium, tantalum and their alloys.

8. Electromechanical transducer according to claim 5, wherein the transducer housing is produced at least partially from a bio-compatible ceramic material.

9. Electromechanical transducer according to claim 1, wherein the membrane consists of biocompatible material.

10. Electromechanical transducer according to claim 9, wherein the material of the membrane is a metallic material selected from the group consisting of titanium, niobium, tantalum and their alloys.

11. Electromechanical transducer according to claim 1, wherein the housing has a circular cross section and has a diameter in the range of 6 to 13 mm.

12. Electromechanical transducer according to claim 1, wherein the piezoelectric ceramic disk is applied to an inner side of the membrane as an electromechanically active element.

13. Electromechanical transducer according to claim 1, wherein the piezoelectric ceramic disk is circular.

14. Electromechanical transducer according to claim 1, wherein the piezoelectric ceramic disk consists of lead-zirconate-titanate (PZT).

15. Electromechanical transducer according to claim 1, wherein the thickness of the membrane and the thickness of the piezoelectric ceramic disk are approximately the same.

16. Electromechanical transducer according to claim 1, wherein the thickness of the membrane and the thickness of the piezoelectric ceramic disk are each in the range of 0.05 mm to 0.15 mm.

17. Electromechanical transducer according to claim 1, wherein the membrane has a radius that is greater than that of the piezoelectric ceramic disk by a factor of 1.2 to 2.0.

18. Electromechanical transducer according to claim 17, wherein the radius of the membrane is greater than the radius of the piezoelectric ceramic disk by a factor of about 1.4.

19. Electromechanical transducer according to claim 1, wherein both the membrane and the housing are electrically conductive; wherein the piezoelectric ceramic disk is electrically connected with the membrane; and wherein the housing forms one of two electrical connections of the transducer.

20. Electromechanical transducer according to claim 19, wherein the piezoelectric ceramic disk and the membrane are connected to one another by an electrically conductive bonding.

21. Electromechanical transducer according to claim 1, wherein the bow for transmitting the membrane oscillations to the coupling element is generally L-shaped and is attached with a short leg in an area of the center of the membrane, and a long leg of the bow running at a distance from and approximately parallel to the membrane with an end of the long leg projecting a short distance beyond an outside edge of the housing.

22. Electromechanical transducer according to claim 21, wherein the short distance that the long leg projects beyond the outside edge of the housing is about 2 mm.

23. Electromechanical transducer according to claim 1, wherein the bow is produced from a material which is selected from the group consisting of a metallic solid, a hollow metal wire and a carbon fiber reinforced composite material.

24. Electromechanical transducer according to claim 1, wherein the diameter of the bow is in the range of 0.25 to 1.00 mm.

25. Electromechanical transducer according to claim 1, wherein a stirrup prosthesis is mechanically permanently attached to an oscillating distal end of the transducer bow for direct inner ear stimulation.

26. Electromechanical transducer according to claim 1, wherein a sleeve is mechanically permanently attached to an oscillating distal end of the transducer bow by a wire hook, which is adapted to be mounted on the stirrup head of the user's ear for direct mechanical stimulation of the stirrup.

27. Electromechanical transducer according to claim 26, wherein the sleeve is produced from a material which is selected from the material group consisting of polyethylene, polytetrafluoroethylene and hydroxylapatite.

28. Electromechanical transducer according to claim 26, wherein the wire hook is formed of a metallic material which is selected from the material group consisting of platinum, platinum alloys, titanium, titanium alloys, niobium, niobium alloys and high-grade steel.

29. Electromechanical transducer according to claim 1, wherein one hook part of a double hook is mechanically permanently attached to an oscillating distal end of the transducer bow and wherein the other hook part is adapted, in the manner of a stirrup prosthesis, to be looped around the long anvil projection of the wearer's ear to transmit the oscillations from the bow to the anvil of the wearer's ear.

30. Electromechanical transducer according to claim 29, wherein the double hook is produced from a metallic material which is selected from the material group consisting of platinum, platinum alloys, titanium, titanium alloys, niobium, niobium alloys and high-grade steel.

31. Electromechanical transducer according to claim 1, wherein the mechanical properties of an oscillatory system formed of the membrane, the bow and the coupling element are selected and matched as a means for causing the oscillatory system to have a first mechanical resonant frequency in the range of 6 to 12 kHz.

32. Electromechanical transducer according to claim 31, wherein the mechanical properties of the oscillatory system is selected and matched so that its first mechanical resonant frequency is at about 10 kHz.

33. Electromechanical transducer according to claim 1, wherein the mechanical properties of the membrane are selected so that a mechanical output impedance of the transducer is above a mechanical load impedance of the transducer when oscillations of the transducer are coupled to said one of the middle ear and the inner ear, and movement of the coupling element is load independent.

34. Electromechanical transducer according to claim 1, wherein for controlling a portion of sound energy radiated by oscillation of the membrane, a cover is locked on an upper side of the transducer housing; wherein said cover has a U-shaped slot with an output opening; and wherein the bow is received in said U-shaped slot.

35. Electromechanical transducer according to claim 34, wherein the cover has at least one deformable clamp on its upper side with, said clamp being deformed after adaptively positioning the transducer housing in the user's ear as a means for providing a permanent and long-term stable attachment against a superimposed surface of an artificial mastoid cavity.

36. Electromechanical transducer according to claim 35, wherein the clamp is wire-shaped and is produced from a material which is selected from the material group consisting of platinum, platinum alloys, titanium, titanium alloys, niobium, niobium alloys and high-grade steel.

37. Electromechanical transducer according to claim 4, wherein an underside of the housing is coated with a bioactive layer adapted grow together with the bone of the bottom of the artificial mastoid cavity after positioning of the transducer in the user's ear as a means for assuring a long-term stable, mechanically permanent attaching of the transducer in the user's ear.

38. Electromechanical transducer according to claim 1, comprising holding means consisting of a bioactive material adapted to grow together with the bone of the bottom of an artificial mastoid cavity as a means for assuring a long-term stable, mechanically permanent attaching of the holding means in the user's ear, said transducer housing being adapted to be mechanically solidly and replaceably attached to said holding means.

* * * * *